United States Patent
Fischer et al.

(10) Patent No.: US 10,711,041 B2
(45) Date of Patent: *Jul. 14, 2020

(54) LYOPHILISATE CONTAINING A CYCLIC PEPTIDE OF FORMULA $X_1$-GQRETPEGAEAKPWY-$X_2$

(71) Applicant: APEPTICO FORSCHUNG UND ENTWICKLUNG GMBH, Vienna (AT)

(72) Inventors: Bernhard Fischer, Vienna (AT); Rudolf Lucas, Martinez, GA (US)

(73) Assignee: APEPTICO FORSCHUNG UND ENTWICKLUNG GMBH, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 14/784,926

(22) PCT Filed: Apr. 18, 2014

(86) PCT No.: PCT/EP2014/058010
§ 371 (c)(1),
(2) Date: Oct. 15, 2015

(87) PCT Pub. No.: WO2014/173842
PCT Pub. Date: Oct. 30, 2014

(65) Prior Publication Data
US 2016/0083431 A1    Mar. 24, 2016

(30) Foreign Application Priority Data

Apr. 23, 2013 (EP) .................................. 13164829

(51) Int. Cl.
| | | |
|---|---|---|
| *A61K 9/72* | (2006.01) | |
| *A61K 38/12* | (2006.01) | |
| *C07K 7/64* | (2006.01) | |
| *A61K 38/19* | (2006.01) | |
| *A61K 9/00* | (2006.01) | |

(52) U.S. Cl.
CPC .............. *C07K 7/64* (2013.01); *A61K 9/0073* (2013.01); *A61K 38/12* (2013.01); *A61K 38/191* (2013.01)

(58) Field of Classification Search
None
See application file for complete search history.

(56) References Cited

U.S. PATENT DOCUMENTS

| 2007/0299003 A1* | 12/2007 | Schaefer | A61K 38/191 514/1.5 |
| 2009/0325958 A1* | 12/2009 | Navratil | A61K 31/4025 514/236.5 |
| 2013/0072444 A1* | 3/2013 | Fischer | C07K 14/525 514/21.1 |
| 2013/0261048 A1* | 10/2013 | Fischer | A61K 38/191 514/3.7 |

FOREIGN PATENT DOCUMENTS

| WO | WO2006013183 | 2/2006 | | |
| WO | WO2010099556 | 9/2010 | | |
| WO | WO2011085423 | 7/2011 | | |
| WO | WO 2011/160664 | * 12/2011 | ............. | A61K 38/19 |
| WO | WO 2012/065201 | * 5/2012 | ............. | A61K 38/19 |

OTHER PUBLICATIONS

Lucas, R., et al. Science. (1994). 263; pp. 814-817.*
Applied Biosystems Technical Bulletin; May 1998; pp. 1-12.*
IPRP cited in Patent Application No. PCT/EP2014/058010 dated Nov. 5, 2015.
Allison et al., "Hydrogen Bonding between Sugar and Protein is Responsible for Inhibition of Dehydration-Induced Protein Unfolding", Archives of Biochemistry and Biophysics, vol. 365, Issue 2, May 15, 1999, pp. 289-298.
Baginski et al., "In vitro and in vivo characterisation of PEG-lipid-based micellar complexes of salmon calcitonin for pulmonary delivery", Pharm Res. Jun. 2012;29(6):1425-34. doi: 10.1007/s11095-012-0688-6. Epub Feb. 10, 2012.
Chang et al., "Mechanisms of protein stabilization in the solid state", J Pharm Sci. Sep. 2009; 89(9): 2886-908. doi: 10.1002/jps.21825.
Elia Nadia et al: "Functional identification of the alveolar edema reabsorption activity of murine tumor necrosis factor-alpha", American Journal of Respiratory and Critical Care Medicine, American Lung Association, New York, NY, US, vol. 168, No. 9, Nov. 1, 2003, pp. 1043-1050, XP002455314.
Hamill et al: Improved Patch-Clamp Techniques for High-Resolution Current Recording from Cells and Cell-Free Membrane Patches Pflugers Arch. 1981, 391(2):85-100., 1981.
Hazemi et al: "Essential structural features of TNF-alpha lectin-like domain derived peptides for activation of amiloride-sensitive sodium currecnt in A549 cells", Journal of Medicinal Chemistry, American Chemical Society, vol. 53, No. 22, Oct. 27, 2010, pp. 8021-8029, XP002638326.

(Continued)

*Primary Examiner* — Kevin S Orwig
(74) *Attorney, Agent, or Firm* — Workman Nydegger

(57) ABSTRACT

Cyclic peptide of formula $$X_1\text{-GQRETPEGAEAKPWY-}X_2,$$

wherein $X_1$ comprises an amino acid (sequence), with 1 to 4 members, comprising natural and unnatural amino acids, and $X_2$ comprises a natural amino acid, and wherein $X_1$ comprises the N-terminal amino acid left in position 1, and $X_2$ the C-terminal amino acid in the ultimate, right position, in the form of a lyophilisate without additives and/or stabilizers and its use.

11 Claims, 6 Drawing Sheets
Specification includes a Sequence Listing.

(56) References Cited

OTHER PUBLICATIONS

Lee et al., "Intrapulmonary potential of polyethylene glycol-modified glucagon-like peptide-1s as a type 2 anti-diabetic agent", Regulatory Peptides, vol. 152, Issues 1-3, Jan. 8, 2009, pp. 101-107.
Morris et al., "Pegylation of Antimicrobial Peptides Maintains the Active Peptide Conformation, Model Membrane Interactions, and Antimicrobial Activity while Improving Lung Tissue Biocompatibility following Airway Delivery", Antimicrob Agents Chemother. Jun. 2012; 56(6): 3298-3308. doi: 10.1128/AAC.06335-11, PMCID: PMC3370748.
Patton et al., "Inhaling medicines: delivering drugs to the body through the lungs", Nat Rev Drug Discov. Jan. 2007;6(1):67-74.
Roberts et al., "Chemistry for peptide and protein PEGylation", Adv Drug Deliv Rev., Jun. 17, 2002;54(4): 459-76.
Vadasz I et al: "The lectin-like domain of tumor necrosis factor-[alpha] improves alveolar fluid balance in injured isolated rabbit lungs", Critical Care Medicine 200805 US, vol. 36, No. 5, May 2008, pp. 1543-1550, XP009172075.
Veronese et al., "PEGylation, successful approach to drug delivery", Drug Discovery Today, vol. 10, Issue 21, Nov. 1, 2005, pp. 1451-1458.

\* cited by examiner

LYOPHILISATE CONTAINING A CYCLIC PEPTIDE OF FORMULA X₁-GQRETPEGAEAKPWY-X₂

The present invention relates to a pharmaceutically applicable lyophilisate, which is assigned for the administration into the lung of a mammal, e.g. of a human.

The activity of pharmaceutically active ingredients rather essentially depends upon the mode how these active ingredients get into the body or into the organ to be treated, respectively.

The most common mode of administering a medicament is parenteral administration. There a medicament is injected through the skin, e.g. directly into the bloodstream, into a muscle, or directly under the skin.

Another common form of intake of medication consists in oral administration into the stomach and intestinal tract. The active ingredients contained in the medicaments are liberated in the stomach and intestinal tract and attain via resorption into the body, the blood and the organs.

Medicaments also may be administered via skin or mucosa.

As an alternative to injection, methods of oral inhalation were suggested. Thereby, medicaments are delivered into the mouth and pharynx in powder form, as well as in the form of droplets which possibly reach the lung room with the breathing air. From there these medicaments are delivered via the pulmonary tissue into the blood and thus are fed systemically to the body.

However, oral inhalation of medicaments still poses a substantial technical problem today. In particular active ingredients with high molecular weight, such as for example proteins, can be applied via oral inhalation only very restricted. By heat and pressure during atomizing or spraying processes proteins as active ingredients are damaged or inactivated physically. Active protein ingredients are rather unstable, both during their storage before and during oral inhalation. In addition, such peptide active ingredients may already be degraded in the lung air space.

To counteract this in such preparations for inhalation of proteins highly diverse pharmaceutical formulations were developed. Thus, such preparations for inhalation of proteins may contain salts, like calcium or sodium salts, stabilizers and tensides, specific buffer mixtures, lipid admixtures and others, for the attainment of desired dissolving characteristics, for warranty of stability, for protecting the activity of the protein. Other admixtures during production of protein medicaments comprise for example albumin, osmotic agents, antioxidants, chemical substances for avoiding aggregation and precipitation, liposomes, gelatine, alginates, sugars and so on.

Thus produced and pharmaceutically processed peptide and protein agents for inhalation then arrive in the blood via lung tissue, either wilfully, or accidentally, and may there be detected.

In summary there are only two internationally registered protein/peptide based medicaments for inhalation at the moment, namely Pulmozyme® (desoxyribonuclease) and Exubera® (insulin). For warranty of activity and stability these preparations contain for example salts (sodium chloride, calcium chloride, or sodium citrate, manitol, glycerol, sodium hydroxide, respectively).

A usual technical way for producing protein/peptide formulations for human medicinal use is lyophilisation (e.g. J Pharm Sci. 2009 September; 98(9): 2886-908). However, during these state-of-the-art processes auxiliaries, such as e.g. disaccharides, are added for ensuring stability and activity of the peptides (Allison S D et al, Arch Biochem Biophys. 1999 May 15; 365(2):289-98). Beyond that it has proved to be successful to bind polyethylene glycol (PEG) onto peptides and proteins, for ensuring activity and stability after water removal during lyophilisation (Roberts et al, Adv Drug Deliv Rev. 2002 Jun., 17; 54(4): 459-76 2002, Morris et al, Antimicrob Agents Chemother. 2012 June; 56(6):3298-308. doi: 10.1128/AAC.06335-11), as well as for avoiding degradation by proteolytic processes (Lee et al, Regul Pept. 2009 Jan. 8; 152(1-3):101-7; Baginski et al, Pharm Res. 2012 June; 29(6):1425-34), or for influencing favourably the molecular mass (Veronese & Pasut, Drug Discov Today. 2005 Nov. 1; 10(21):1451-8; Patton & Byron, Nat Rev Drug Discov. 2007 January; 6(1):67-74), respectively.

Now, surprisingly an application form without additives was found for certain peptides which have a positive influence on the lung function, which application form became apparent to be extremely appropriate.

In one aspect the present invention provides a cyclic peptide of formula $$X_1\text{-GQRETPEGAEAKPWY-}X_2, \quad \text{I}$$

wherein $X_1$ comprises an amino acid (sequence), with 1 to 4, in particular 1 to 3 members, comprising natural and unnatural amino acids, in particular selected from the amino acid (sequence) C (Cys), KSP (Lys-Ser-Pro), K (Lys), ornithine, 4-aminobutyric acid, β-alanine, and $X_2$ comprises a natural amino acid, in particular selected from the group C (Cys), D (Asp), G (Gly) and E (Glu), and wherein $X_1$ comprises the N-terminal amino acid left, in position 1, and $X_2$ the C-terminal amino acid in the ultimate, right position, in the form of a lyophilisate without additives and/or stabilizers.

A lyophilisate provided by the present invention is herein designated also as, lyophilisate of the present (under, according to the present) invention". A peptide in a lyophilisate according to the present invention is herein designated also as, peptide of the present (under, according to the present) invention".

In a lyophilisate of the present invention one or several cyclic peptides of formula I may be present, whereby preferably only one peptide of formula I is present.

A cyclic compound of formula I is the cyclised compound having the amino acid sequence $$X_1\text{-Gly-Gln-Arg-Glu-Thr-Pro-Glu-Gly-Ala-Glu-Ala-Lys-Pro-Trp-Tyr-}X_2, \quad \text{I}$$

wherein $X_1$ and $X_2$ are as defined above.

Novel compounds of formula I also are subject of the present invention.

The ring in a compound of formula I may be formed via binding between two appropriate substituents in two of the amino acid residues of a compound of formula I, e.g. via an amine bond, or a disulfide bridge, whereby the ring preferably comprises at least 15, more preferably at least 17, up to 19 or 20, for example 17 to 19 amino acid residues, which are present in a compound of formula I as ring members.

Preferably formation of the ring is formed by a bond between an appropriate substituent in an amino acid in $X_1$, preferably in the amino acid in position 1 in $X_1$, with an appropriate substituent in $X_2$.

Natural amino acids which may be used in an amino acid sequence of formula I of the present invention are known and comprise for example G (Gly), A (Ala), V (Val), L (Leu), I (Ile), M (Met), P (Pro), F (Phe), W (Trp), S (Ser), T (Thr), N (Asn), Q (Gln), C (Cys), U (Sec), Y (Tyr), D (Asp), E (Glu), H (His), K (Lys), R (Arg).

Unnatural amino acids which may be used in an amino acid sequence of formula I of the present invention comprise
(i) amino acids, having in principle the chemical structure of natural amino acids, however, which are different from alpha amino acids,
(ii) natural amino acids in the D-form, namely other than in the natural L-form, that means natural amino acids, wherein the alkyl group at the C-atom in position 2 is present not in the L-configuration, but in the D-configuration,
(iii) non-natural amino acids, for example others than such as defined under (i) and (ii) above, comprise from 2 to 12, such as from 2 to 6 carbon atoms, at least one amine group, for example one, or two, and at least one carboxy group, for example one or two, optionally beside substituents, which are present also in natural amino acids, e.g. OH, —$CONH_2$, —NH—C(=$NH_2$)$NH_2$, SH, ($C_{1-4}$) alkyl-S—, phenyl, heterocyclyl, e.g. comprising 5 or 6 ring members and comprising at least one heteroatom, for example one or two, selected from N, O, S, preferably N, optionally annellated with a further ring, such as phenyl, e.g. comprising prolyl, indolyl, imidazolyl.

Non-natural amino acids of formula I of the present invention comprise ornithine, 4-amino butyric acid, β-alanine.

In a further aspect, a cyclic compound of formula I of the present invention comprises
a compound having the amino acid sequence SEQ ID NO:1

Cyclo(CGQRETPEGAEAKPWYC)

wherein a disulfide bridge is formed between both of the terminal cysteine residues;
a compound having the amino acid sequence SEQ ID NO:2

Cyclo(KSPGQRETPEGAEAKPWYE)

wherein an amide bond is formed between the amine group which is attached to the ε-carbon atom of the N-terminal lysine residue and the side chain carboxy group, attached to the γ-carbon atom of the C-terminal glutaminic acid residue;
a compound having the amino acid sequence SEQ ID NO:3

Cyclo(KGQRETPEGAEAKPWYG)

wherein an amide bond is formed between the amine group which is attached to the ε-carbon atom of the side chain of the N-terminal lysine residue with the carboxy group of the C-terminal glycine residue;
a compound having the amino acid sequence SEQ ID NO:4

Cyclo(ornithine-GQRETPEGAEAKPWYG)

wherein an amide bond is formed between the amine group which is attached to the δ-carbon atom of the side chain of the N-terminal ornithin residue and the carboxy group of the C-terminal glycine residue;
a compound having the amino acid sequence SEQ ID NO:5

Cyclo(4-amino butyric acid-GQRETPEGAEAKPWYD)

wherein an amide bond is formed between the amine group of the N-terminal 4-amino butyric acid residue and the side chain carboxy group which is attached to the β-carbon atom of the C-terminal asparaginic acid residue;
and
a compound having the amino acid sequence SEQ ID NO:6

Cyclo(β-alanine-GQRETPEGAEAKPWYE)

wherein an amide bond is formed between the amine group of the N-terminal β-alanine residue (3-amino propanoic acid residue) and the side chain carboxy group, which is attached to the γ-carbon atom of the C-terminal glutaminic acid residue.

In the compounds of formula I, as well as in the compounds of the amino acid sequences SEQ ID NO:1, SEQ ID NO:2, SEQ ID NO:3, SEQ ID NO:4, SEQ ID NO:5 or SEQ ID NO:6 the amino acids are normal peptidically connected, with the exception of that bond which leads to the ring formation.

A cyclic compound of formula I is designated herein also as "cyclic compound(s) of the present (under, according to the present) invention" and comprises a cyclic compound of formula I in any form, for example in free form and in the form of a salt. In biological environment normally a compound of formula I is present in the form of a salt.

In a further aspect a compound of formula I in a lyophilisate of the present invention is in form of a salt.

Such salts comprise preferably pharmaceutically acceptable salts, although pharmaceutically unacceptable salts are included, e.g. for the purpose of preparation/isolation/purification.

In biological environment a salt of a compound of formula I normally is a hydrochloride.

A cyclic compound of formula I of the present invention in free form may be converted into a cyclic compound of formula I in salt form and vice versa.

A cyclic compound of formula I of the present invention may be in the form of isomers and isomeric mixtures; e.g. optical isomers. A cyclic compound of formula I may comprise, for example asymmetric carbon atoms and therefore can be in the form of enantiomers, diastereoisomers and mixtures thereof, e.g. racemates. A cyclic compound of formula I may be present in (R)-, (S)- or (R,S)-configuration, preferably in the (R)- or (S)-configuration relating to individual substituents at asymmetric carbon atoms. Isomeric mixtures appropriately may be separated, e.g. according to, such as analogously to a conventional method to obtain pure isomers. The present invention comprises a cyclic compound of formula I in any isomeric form and in any form of isomeric mixtures. In case of natural amino acids the configuration of substituents is normally such, as in natural amino acids.

A cyclicd compound of the present invention may be prepared as appropriate, e.g. according, e.g. analogously, to a method as conventional, or as specified herein, e.g. by solid-phase peptide synthesis, optionally according to the fluorenylmethoxycarbonyl/t-butyl protection strategy on 2-chlorotritylchloride resin using appropriate coupling agents, such as diisopropyl carbodiimide and/or N-hydroxybenzotriazole and appropriate solvent, e.g. N,N-dimethylformamide. Protected amino acids may be coupled in succession to the peptide chain, starting with the C-terminal amino acid. Deprotection of fluorenylmethoxycarbonyl-protected groups may be carried out with a base, e.g. piperidine, such as 20% piperidine in appropriate solvent, such as N-N-dimethyl formamide. The cleavage of the completed, optionally (partially) protected peptide from the resin may be carried out as appropriate, e.g. with the aid of an acid, such as acetic acid in appropriate solvent, e.g. halogenated hydrocarbon, such as $CH_2Cl_2$, e.g. in a 1:1 mixture of acetic acid and $CH_2Cl_2$.

In the case of cysteine-containing peptides, after cleavage from the resin, side-chain deprotection may be carried out, if necessary, e.g. with a strong acid, such as trifluoroacetic acid (TFA), e.g. 95% TFA/5% $H_2O$. Cyclization to obtain a disulfide bond may be carried out by oxidation of terminal cysteine residues, e.g. achievable by aeration of the crude linear peptide at pH 8.5 for 90 hours. Crude peptide product obtained may be purified, e.g. by chromatography, e.g. by reverse phase medium pressure liquid chromatography (RP-MPLC) on an appropriate column, such as an RP-C18-silica gel column, conveniently using an eluent gradient, such as a gradient of 5% to 40% acetonitril-water gradient. A trifluoracetate counter-ion may be replaced, e.g. by acetate, e.g. over a column, such as over a Lewatit MP64 column (acetate form). Following a final washing with water, the purified peptide may be lyophilized as acetate salt and may be obtained in the form of a light coloured, e.g. white powder.

In the case of cysteine-free peptides, the cyclization step may be carried out as appropriate, e.g. still on the partially-protected linear peptide, following cleavage from the resin. After selective cyclization of the cysteine-free peptide, side-chain deprotection in TFA, if necessary, may be carried out. A purification step may be carried out, e.g. via chromatography, e.g. by preparative RP-MPLC. In the peptide thus obtained replacement of the trifluoroacetate ion by acetate may be carried out, e.g. as described above. Lyophilisation of the acetate form of the peptide may also be carried out, e.g. as for cysteine-containing peptides.

The molecular masses of peptides obtained may be confirmed by electrospray ionisation mass spectrometry or MALDI-TOF-MS. E.g., by analytical high performance liquid chromatography purity may be determined.

Cyclic compounds of formula I comprise compounds with the amino acid sequence SEQ ID NO:1, SEQ ID NO:1, SEQ ID NO:2, SEQ ID NO:3, SEQ ID NO:4, SEQ ID NO:5 or SEQ ID NO:6. Such compounds are known, e.g. from Hazemi P., Tzotzos, S. Fischer B., Andavan, G. S. B., Fischer H., Pietschmann H, Lucas, R. and Lemmens-Gruber, R. in J Med Chem. 2010 Nov. 25, 53(22): 8021-8029, "Essential structural features of TNF-α lectin-like domain derived peptides for activation of amiloride-sensitive sodium current in A549 cells" as activating "the amilorid-sensitive epithelial sodium channel (ENaC)" and thus as useful for the treatment of diseases in the lung. By activation of the amilorid-sensitive Sodium Ion Channel (ENaC) it comes to the transport of sodium ions through the lung tissue. An osmotic gradient is formed which leads to passive water transport. If that model is transferred onto the lung, the activation of the amilorid-sensitive Sodium Ion Channel may for example be used for the reduction of water accumulation in the lung, e.g. in the case of pulmonal edema.

In the course of development of the present invention it was found that an active or passive transport of the cyclic peptides of formula I of the present invention wherein $X_1$ and $X_2$ are as defined above, for example having the amino acid sequence SEQ ID NO:1 to SEQ ID NO:6, through the lung tissue into the blood is not desirable and should not happen, because it contributes substantially to the physiological activity of the cyclic peptides having the amino acid sequence SEQ ID 1 to SEQ ID 6, if these attain via oral inhalation in the air room of the lung, such that they deposit at the surface of the lung tissue and there can activate the apical oriented amilorid-sensitive sodium ion channel.

It could be shown surprisingly (example 10) that after inhalation of an aerosol which was prepared from a lyophilisate according to the present invention by addition of water, a peptide of the present invention could not be detected in the blood.

Inhalative preparations were and are normally developed for passing over after inhalation via the lung tissue into the blood stream, thus possibly avoiding a parenteral injection. The target of previous inhalation medicaments namely is systemic activity. Via distribution of an agent in the blood the molecule gets into each tissue and organ. A substantial disadvantage of systemic application, however, is the great spectrum regarding toxicity and side effects at organs and tissue in the body, which are not associated with the disease to be treated.

When administering an aqueous aerosol, prepared from a lyophilisate of the present invention in contrast to that the peptides get into the barrier between air and lung epithet where they activate a sodium channel. The peptides of the present invention thus operate "locally" onto the epthelian tissue of the lung and not systemically. A step of the peptides through the lung tissue is not desired and also does not happen.

In contrast to the peptide formulations known from literature, it could be succeeded via the aqueous aerosol, prepared from a lyophilisate of the present invention and which does not contain additives, to avoid a spreading of the inhaled peptides through the lung into the blood. By that the extremely positive effect is obtained that possible systemic-toxic characteristics of the peptide can be avoided—also onto other organs than the lung.

Otherwise usual side effects thus may be excluded which provides great medicinal benefit. By local administration onto the inner lung surface and without diffusion into the blood marked less active agent is necessary compared with systemic application.

Furthermore, surprisingly it became apparent that in a lyophilisate according to the present invention comprising cyclic peptides of formula I, in particular the cyclic peptides of amino acid sequences SEQ ID NO: 1 to SEQ ID NO:6 without additives, chemical and biological instability practically can be excluded over months and years. Namely it came apparent that the chemical structure and the biological activity of the cyclic peptides of formula I of the present invention, as those of amino acid sequences SEQ ID NO: 1 to SEQ ID NO:6, are not damaged, surprisingly also without commonly used additives and/or stabilizers.

Upon administration of the cyclic peptides of formula I of the present invention, in particular of amino acid sequences SEQ ID NO: 1 to SEQ ID NO:6 for inhalation it became apparent, that the cyclic peptides are constituted such, that they are also stable for longer time in dissolved form, namely in aqueous solution, also without additives, for example in a storage container of a device for spraying (nebulizer). In addition it has turned out that the cyclic peptides of formula I of the present invention, in particular of amino acid sequences SEQ ID NO: 1 to SEQ ID NO:6 of the present invention, can be prepared in such a way that upon transformation into an inhalable form the cyclic proteins of SEQ ID NO: 1 to SEQ ID NO:6 are not damaged and thus keep full activity, surprisingly also without adding commonly used additives and/or stabilizers.

For the preparation of a solution of, e.g. at least one, of the peptides of formula I of the present invention, in particular of SEQ ID NO: 1 to SEQ ID NO:6 in the form which is appropriate for spraying, these peptides may be dissolved in water and the solution obtained may be lyophilized, for example without further additives, as e.g. commonly used additives and/or stabilizers, thereby obtaining a powder. Before lyophilisation the solution optionally may be filtered in order to remove turbidities.

In a further aspect the present invention provides the use of a lyophilisate according to the present invention for the preparation of an aerosol which is appropriate for spraying, in particular an aerosol without additives and/or stabilizers.

The use of a lyophilisate according to the present invention is herein also designated as "Use according to (of) the present invention".

It was found that the peptides of formula I, in particular those of SEQ ID NO: 1 to SEQ ID NO:6 in such lyophilized form were stable in cooled environment for at least 24 months and at room temperature for at least 6 months, even without the addition of otherwise usual additives and/or stabilizers.

A lyophilisate according to the present invention may be dissolved in water for administration to obtain an aerosol, for example with or without additives, e.g. without additives, e.g. for direct preparation of an aerosol, or for storage as solution, e.g. in a storage container.

In a further aspect the present invention provides the use of a lyophilisate, wherein a peptide of formula I, wherein $X_1$ and $X_2$ are as defined above, is present in aqueous solution, in particular without additives and/or stabilizers.

It became surprisingly and advantageously apparent that the thus dissolved cyclic peptides of formula I, wherein $X_1$ and $X_2$ are as defined above, in particular of amino acid sequences SEQ ID NO: 1 to SEQ ID NO:6, are stable in solution for at least 7 days, that means that the biological activity of the cyclic proteins was not diminished when transforming into the inhalable shape, even without the addition of otherwise usual additives and/or stabilizers.

Upon application of the cyclic peptides of the present invention, in particular of amino acid sequences SEQ ID NO: 1 to SEQ ID NO:6, it has turned out that a solution of the peptides is constituted such, that it can be converted into an aerosol, e.g. by means of an nebulizer, by which the cyclic peptides are sprayed. Thereby it has turned out that aerosol particles were obtained having a diameter of less or equal 5 μm.

It furthermore became apparent that an aerosol, which predominantly comprises droplets having a diameter of ≤5 μm is particularly appropriate for administration, because as a consequence the aerosol arrives in the air room in the lung. The lower limit of the droplet size simply comes along with the feasibility of the droplet size.

In a further aspect the present invention provides the use of a lyophilisate for the preparation of an aerosol, wherein the particle size has a diameter of ≤5 μm.

In a further aspect the present invention provides the use of a lyophilisate according to the present invention, which is characterized in that the aerosol which is prepared from the lyophilisate is used for improving/conditioning the lung function in the form of inhalation.

In a further aspect the present invention provides the use of an aerosol, prepared from a lyophilisate according to the present invention, in particular an aerosol without additives, for the improvement of the lung function, e.g. for the treatment of pulmonal edema, and in a further aspect.

a process for improving the lung function, e.g. for the treatment of pulmonal edema, which is characterized in that an aerosol according to the present invention without additives is administered to a patient in the form of an inhalation;

and in a further aspect, a lyophilisate according to the present invention for use for improving/conditioning the lung function, or for inhalation for improving/conditioning the lung function.

The appropriate dose depends on different factors, for example from the chemical nature and the pharmacokinetic properties of a cyclic compound of formula I, the individual host, e.g. the body weight therefrom, the age and the individual condition of a patient and the nature and severity of the disease. However, in general, for satisfactory results in larger mammals, for example humans, one can emanate that a (daily) dosage of (ca.) 0.1 mg/kg body weight to approximately (ca.) 200 mg/kg, for example 1 mg/kg body weight up to 100 mg/kg body weight, administered for example in several, e.g. up to 4 (partial) dosages, will deliver successful results. Children usually obtain half of the dose of an adult.

Investigations further have shown that by treatment of a donor lung ex vivo, namely before transplantation into a patient, with a cyclic peptide of formula I, wherein $X_1$ and $X_2$ are as defined above, in particular having the amino acid sequence of SEQ ID NO:1 to SEQ ID NO:6, surprisingly improves/conditions lung functions. Thereby it was shown, that an exceeding improvement could be achieved, if the lung to be transplanted was treated before transplantation with an aerosol from a lyophilisate of the present invention, in particular without additives.

In a further aspect the present invention provides an extracorporeal method of conditioning/improving lung functions, which is characterized in that a donor lung is sprayed with an aqueous aerosol ex vivo, which is in particular prepared without additives and/or stabilizers from a lyophilisate according to the present invention.

Treatment of the lung also can (still) take place after ensued transplantation in the recipient.

Thereby results were obtained, as shown in FIG. 1. The concentration of a cyclic peptide of formula I according to the present invention in the aerosol thereby was from 5 nM to approximately 150 nM.

EXAMPLE 1

Peptide Synthesis

Figure 1:
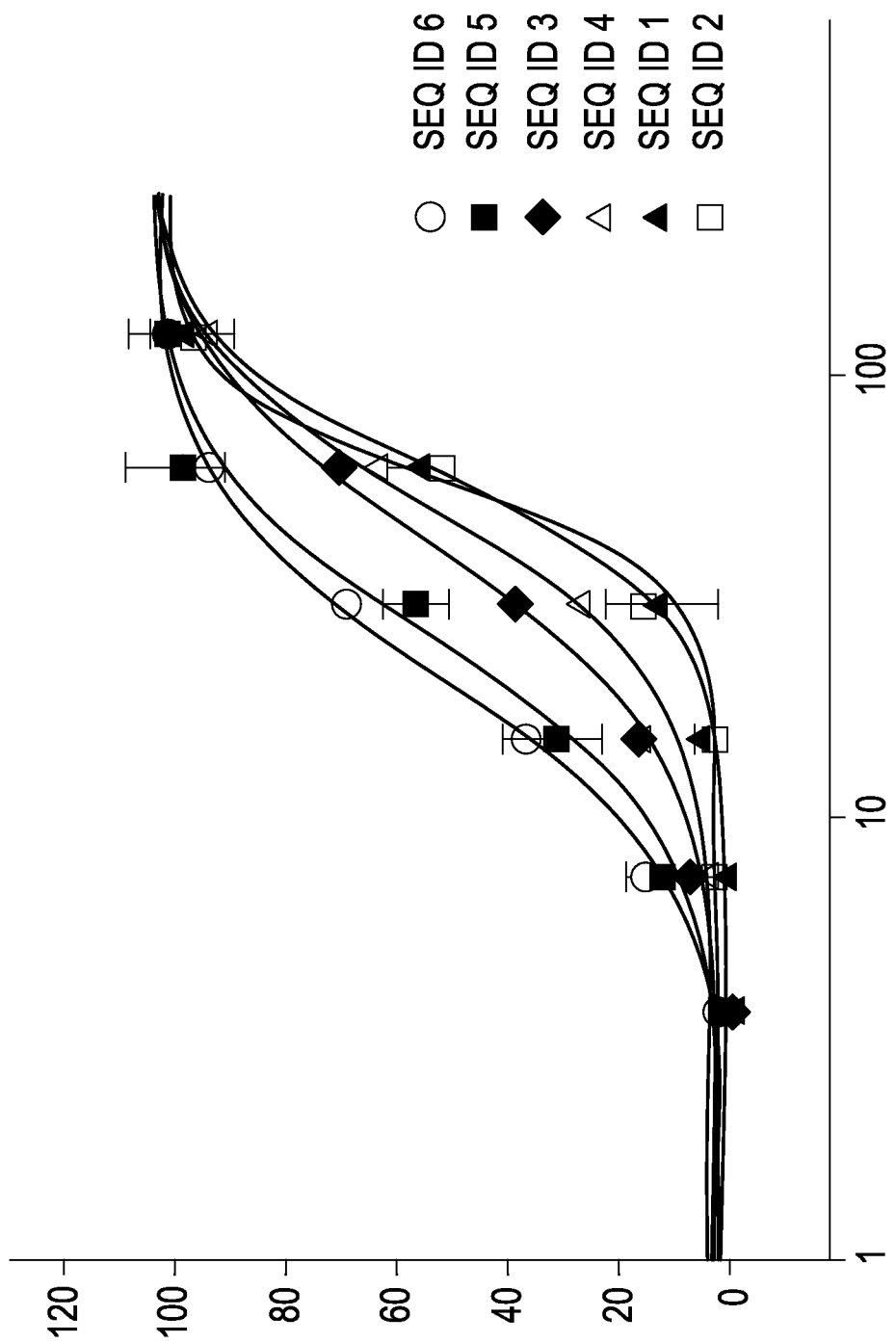
FIG. 1 shows the activity of the cyclic peptide having the amino acid sequence SEQ ID NO:1 to SEQ ID NO:6 in dependence from the concentration. On the x-axis the concentration in nM (logarithmic scale) of the cyclic proteins of SEQ ID NO:1 to SEQ ID NO:6 is indicated, on the y-axis the sodium ion flow in %.

Peptides were prepared according to the following steps:
Sequential coupling of the amino acids; selective cleavage from the solid phase; purification and lyophilisation, selective cyclisation; cleavage of the protecting groups; purification and lyophilisation; analytical investigation.

All cyclic peptides of the present invention, the peptides of the amino acid sequences SEQ ID NO:1 to SEQ ID NO:6, as well as the peptide with the amino acid sequence SEQ ID NO:7, were prepared fully automated according to the fluorenylmethoxycarbonyl/t-butyl protection strategy in the form of a solid phase synthesis on a carrier (2-chlorotritylchloride resin). Diisopropyl carbodiimide and N-hydroxybenzotriazole were used as coupling reagents. All coupling steps were carried out in N—N-dimethyl formamide as a solvent. The protected amino acids thereby were sequentially coupled onto the respective C-terminal amino acid which was used as a starting material. Deprotection of fluorenylmethoxycarbonyl was carried out in 20% piperidine in N—N-dimethyl formamide. Cleavage of the completed, partially-protected peptide from the resin was carried out in a 1:1 mixture of acetic acid and dichloromethane.

In the case of cysteine-containing peptides, side-chain deprotection took place after cleavage from the carrier (resin), in 95% trifluoroacetic acid, whereupon cyclisation was performed by oxidation of terminal cysteine residues, achieved by aeration of the crude linear peptide at basic pH (8.5) for 90 hours. The crude cyclic peptide was purified by reverse phase medium pressure liquid chromatography (RP-MPLC) on an RP—C18-silica gel column with a gradient of 5%-40% acetonitril/water. Finally, the trifluoracetate-ion was replaced by acetate on a Lewatit MP64 column (acetate form). Following a wash in water, the purified peptide was lyophilized as an acetate salt and obtained as a white to off-white powder.

In the case of cysteine-free peptides, the cyclisation step was carried out on the partially-protected linear peptide following cleavage from the carrier(resin). After selective cyclisation of the cysteine-free peptides, side-chain deprotection in trifluoroacetic acid was carried out, followed by preparative RP-MPLC chromatography, replacement of the trifluoroacetate ion by acetate and lyophilisation of the acetate form, as for the cysteine-containing peptides.

Thereafter the cyclic proteins of SEQ ID NO:1 to SEQ ID NO:6 were analyzed regarding purity and mass by means of reverse HPLC.

The purity of the cyclic protein of SEQ ID 1 was 96.3%. m/z (ESI) 1924.2 (M++1).

The purity of the cyclic protein of SEQ ID 2 was 96.3%. m/z (ESI) 1924.2 (M++1).

The purity of the cyclic protein of SEQ ID 3 was 98.8%. m/z (ESI) 1888.2 (M++1).

The purity of the cyclic protein of SEQ ID 4 was 97.4%. m/z (ESI) 1873.4 (M++1).

The purity of the cyclic protein of SEQ ID 5 war 99%. m/z (MALDI-TOF) 1901.6 (M++1).

The purity of the cyclic protein of SEQ ID 6 was 99%. m/z (MALDI-TOF) 1902.7 (M++1).

The purity of the cyclic protein of SEQ ID 7 was 95%. m/z (MALDI-TOF) 1778.02 (M++1).

The compound having the amino acid sequence SEQ ID NO:7

Cyclo(CGQREAPAGAAAKPWYC)

wherein a disulfide bridge is formed between both of the terminal cysteine residues, became apparent to be biologically inactive and was used for comparison purposes.

EXAMPLE 2

Electrophysiological Investigations of the Amilorid-Sensitive Sodium Ion Channel (ENaC)

Macroscopic Sodium Ion Currents were derived from human lung epithelian cells A549 in the "whole cell" configuration by means of the "Patch-clamp" technique (Hamill et al, Pflugers Arch. 1981, 391(2):85-100, 1981). For the currents in the "whole cell" configuration the following bath- and electrode solutions were used:

Bath solution: 135 mM sodium methansulfonate, 10 mM NaCl, 2.7 mM KCl, 1.8 mM $CaCl_2$, 2 mM $MgCl_2$, 5.5 mM glucose, and 10 mM HEPES, pH 7.4.

Electrode solution: 120 mM potassium methansulfonate, 15 mM KCl, 6 mM NaCl, 1 mM $Mg_2ATP$, 2 mM Na3ATP, 10 mM HEPES, and 0.5 mM EGTA (pH 7.2).

Cover glasses with thereon cultivated cells were transferred into a 1 ml containing trial bath, fixed onto the microscope table (Axiovert 100, 400-fold enlargement) and the cells were superfunded with the above described bath solution. Subsequent from an appropriate cell (sticking on the cover glass) the current was deduced. For that a microelectrode filled with an electrolyte solution (glass capillary with a defined heat-polished top opening of approximately 1-3 μm—corresponds to an electric resistance of the electrode top of 3-5 MΩ) was attached and the membrane sucked in, so that a "Gigaohm-Seal" between membrane and electrode was formed, in order to minimize the leakage current. At the "whole cell"-configuration the membrane under the electrode top was disrupted, in order to enable measurement of the current which flows through all ion channels of the cell. On receipt of a "Gigaohm-Seal" a defined membrane hold potential was created via a preamplifier (CV-4 Headstag, Axon Instruments) and amplifier (Axopatch 1D, Axon Instr.) and the current which thereby flows through the ion channels is measured.

The pulse protocol consisted in a hyperpolarisation of the cell membrane to −100 mV for 5 seconds and subsequent stepwise depolarisation in 20 mV steps to +100 mV.

That protocol was done before (control) and after addition of the cyclic proteins. The thus obtained currents were recorded and analyzed by means of the program PCLAMP 6.0. For that, the currents obtained under the presence of amilorid were subtracted from the previously recorded currents, with the result that the amilorid-sensitive sodium current by the epithelian sodium channels could be determined.

The results of the measurements are outlined in Table 1, wherein there is indicated the activity of the cyclic proteins of SEQ ID 1 to SEQ ID 7 on the cellular amilorid-sensitive sodium ion current. The activity of the individual peptides is indicated as $EC_{50}$ (in nM). The EC50 is the effective concentration, at which 50% of the maximum activity is measured (that means maximum increase of current intensity I).

TABLE 1

| Cyclic Protein | $EC_{50}$ (nM) |
| --- | --- |
| SEQ ID NO: 1 | 54 |
| SEQ ID NO: 2 | 56 |
| SEQ ID NO: 3 | 38 |
| SEQ ID NO: 4 | 45 |
| SEQ ID NO: 5 | 24 |
| SEQ ID NO: 6 | 19 |
| SEQ ID NO: 7 | no activity |

In FIG. 1, the activity of the cyclic proteins SEQ ID 1 to SEQ ID 7 in dependency from the concentration are plotted. Maximum activity was indicated with 100%.

The investigations shown in Table 1 and in FIG. 1 show that the cyclic peptides having the amino acid sequences SEQ ID NO:1 to SEQ ID NO:6 are biologically active, whereas the cyclic peptide having the amino acid sequence SEQ ID NO:7, which structurally shows a certain similarity, is not active.

EXAMPLE 3

Preparation of the Lyophilisate

Development of a stable storage form of the cyclic peptide of formula I was carried out on technical scale. For that the cyclic peptides of SEQ ID NO:1 to SEQ ID NO:6, as well as of the cyclic peptide of SEQ ID NO:7 were dissolved in pure water in amounts of 0.1 mg/ml to 100 mg/ml and filtered for removal of turbidities, contaminations and possible unsterility through a filter with a pore size of 0.2 μm.

Figure 3:
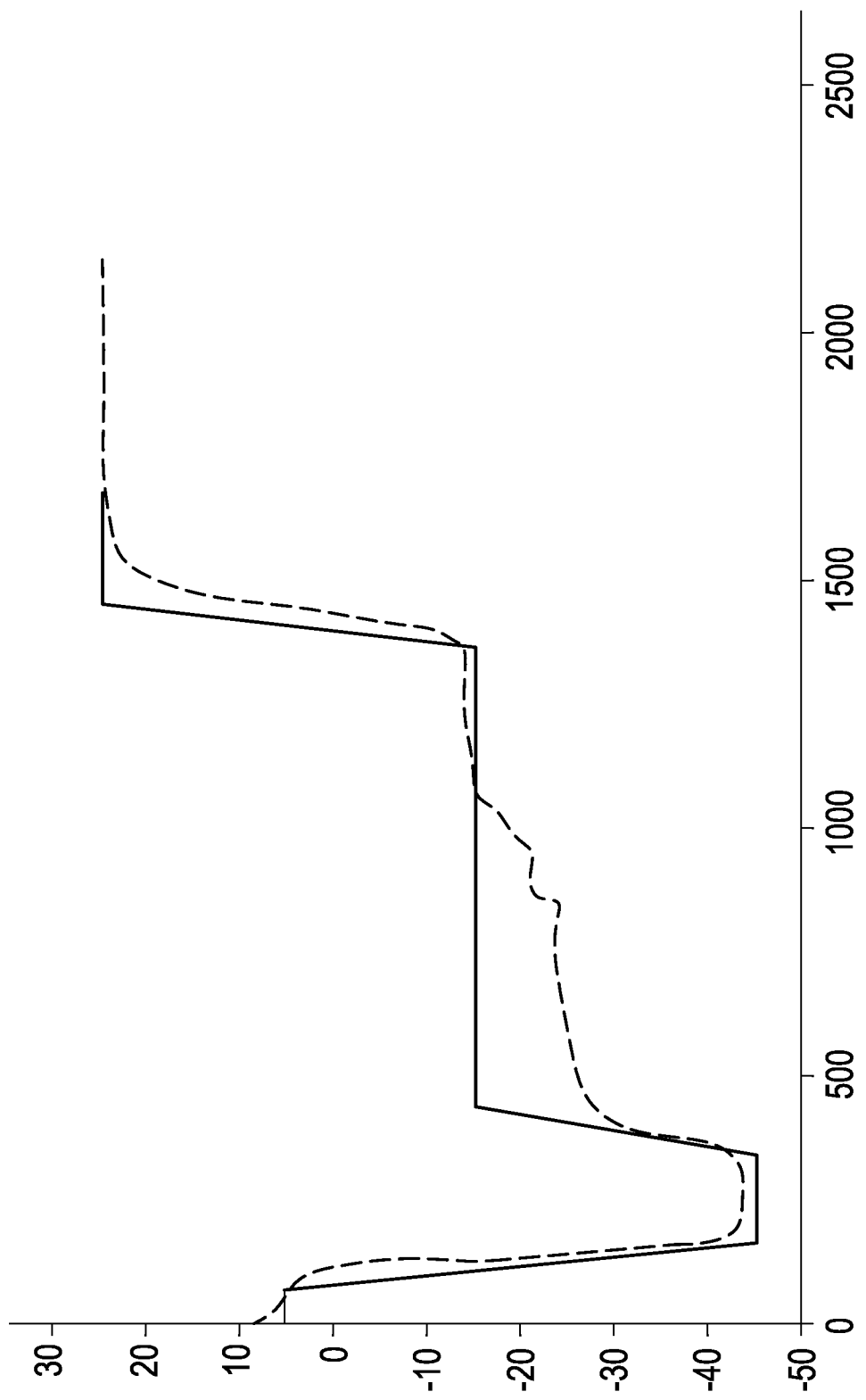
FIG. 3 shows the lyophilisation cycle of the peptides having the amino acid sequences SEQ ID NO:1 to SEQ ID NO:7, plotted as panel temperature (solid line) and product temperature (dotted line) in ° C. (y-axis) with the time in minutes (x-axis).

After filtration the cyclic peptide, dissolved in pure water was portioned into glass or plastic ampoules and by means of freeze-drying (lyophilisation) converted into a stable powder. Thereby the lyophilisation parameters described in Table 2 and the lyophilisation cycle described in FIG. 3 were obtained.

TABLE 2

| Step | Process | Shelf temperature (° C.) | Holding time (min) | Temperature shift (° C.) during Holding Time | Pressure (mTorr) |
| --- | --- | --- | --- | --- | --- |
| 1 | Load | 5 | 60 | 5.0 | n/a |
| 2 | Freezing | −45 | 150 | 0.5 | n/a |
| 3 | Primary Drying | −15 | 940 | 0.3 | 250 |
| 4 | Secondary Drying | 20 | 630 | 0.5 | 75 |
| 5 | Termination | Vial closed under 95% pure nitrogen atmosphere | | | |

As a result of lyophilisation a white powder each was obtained for the cyclic peptides having the amino acid sequence SEQ ID NO:1 to SEQ ID NO:6.

EXAMPLE 4

Stability Investigation of the Lyophilisate from Example 2 after Storage at Room Temperature and in the Refrigerator The stability investigation of the lyophilisates of the cyclic peptides of amino acid sequence SEQ ID NO:1 to SEQ ID NO:6. was done on technical scale. For that the lyophilisate was stored up to 24 months at 2 to 8° C. and up to 6 months at 25° C. at 60% relative humidity. Stability was investigated at different time points during that period. In particular, the appearance, contents, as well as purity of the cyclic peptides were investigated. For that laboratory-common analytical processes were used, such as e.g. visual inspection and reverse HPLC.

In addition, after a storage of 24 months at 2-8° C. the biological activity was determined by means of Patch Clamp experiments. Thereby macroscopic currents of A549 cells were deduced in the "whole cell" configuration of the "Patch-clamp" technique, as described under "Electrophysiological Investigations of the amilorid-sensitive Sodium Ion Channel (ENaC)".

In Table 3 the results of the stability investigations of the respective lyophilisate of the cyclic peptides having the amino sequences SEQ ID NO:1 to SEQ ID NO:6 at time point T=0 and after 6 months (T=6M), or after 24 months (T=24M), respectively, are outlined. The appearance did not change during the whole time period. The contents on cyclic peptides, as well as purity are subject of only minor fluctuations.

TABLE 3

| Analytical Parameter | Storage temperature 2-8° C. | | Storage temperature 25° C./60% rH | |
| --- | --- | --- | --- | --- |
| | T = 0 | T = 24 M | T = 0 | T = 6 M |
| Appearance | | | | |
| SEQ ID 1 | white powder | | white powder | |
| SEQ ID 2 | white powder | | white powder | |
| SEQ ID 3 | white powder | | white powder | |
| SEQ ID 4 | white powder | | white powder | |

TABLE 3-continued

| Analytical | Storage temperature 2-8° C. | | Storage temperature 25° C./60% rH | |
|---|---|---|---|---|
| Parameter | T = 0 | T = 24 M | T = 0 | T = 6 M |
| SEQ ID 5 | white powder | | white powder | |
| SEQ ID 6 | white powder | | white powder | |
| Amount/Contents | | | | |
| SEQ ID 1 | 100% | 99% | 100% | 99% |
| SEQ ID 2 | 100% | 99% | 100% | 99% |
| SEQ ID 3 | 100% | 99% | 100% | 99% |
| SEQ ID 4 | 100% | 99% | 100% | 99% |
| SEQ ID 5 | 100% | 99% | 100% | 99% |
| SEQ ID 6 | 100% | 99% | 100% | 99% |
| Purity | | | | |
| SEQ ID 1 | 96% | 96% | 96% | 95% |
| SEQ ID 2 | 96% | 96% | 96% | 95% |
| SEQ ID 3 | 98% | 98% | 98% | 97% |
| SEQ ID 4 | 97% | 97% | 97% | 96% |
| SEQ ID 5 | 99% | 99% | 99% | 98% |
| SEQ ID 6 | 99% | 99% | 99% | 98% |

The lyophilisate of the cyclic peptides of amino acid sequence SEQ ID NO:1 to SEQ ID NO:6 each is thus stable for up to 24 months at 2 to 8° C. and up to 6 months at 25° C./60% relative humidity.

The biological activity measurement by means of Patch Clamp Experiments revealed that a lyophilisate, each with one of the cyclic peptides of amino acid sequence SEQ ID NO:1 to SEQ ID NO:6, still fully was active after 24 months of storing at 2 to 8° C.

EXAMPLE 5

Production of an Aqueous Solution of Cyclic Peptides of Amino Acid Sequence SEQ ID NO:1 to SEQ ID NO:6 Before Inhalation For pre-preparation for administration of the cyclic proteins of amino acid sequence SEQ ID NO:1 to SEQ ID NO:6, the stable white powders, obtained during lyophilisation according to example 2, were dissolved, each in a defined volume of pure water to obtain a concentration between 0.1 mg pro ml and 100 mg pro ml. The resultant solutions of the cyclic proteins of SEQ ID 1 to SEQ ID 6 were then transferred into the storage containers of the nebulizers. By dissolution of the cyclic peptides of SEQ ID NO:1 to SEQ ID NO: 6 in water clear solutions were obtained.

EXAMPLE 6

Investigations Regarding Stability of the Cyclic Peptides of Amino Acid Sequences SEQ ID NO:1 to SEQ ID NO:6 in Dissolved Preparation Before Inhalation For practical reasons, an aqueous solution of a cyclic peptide of amino acid sequences SEQ ID NO:1 to SEQ ID NO:6 not always can be used directly after its preparation for inhalation. For that reason the stability of an aqueous solution was investigated exemplarily. The ready to use-solution therefore was stored either in a syringe commonly used in laboratory, at 2 to 8° C. for 7 days, or in a container of a nebulizer at 25° C. for 24 hours. In particular the appearance, the contents of cyclic protein of SEQ ID NO:1, as well as the purity thereof were investigated. The methods used therefore were analytical methods commonly used in laboratory, as for example the visual inspection, as well as analysis by means of reverse HPLC.

The results of the stability investigations of an aqueous solution of the cyclic peptide having the amino acid sequence of SEQ ID NO:1 are set out in Table 4. The appearance did not change during the whole time period. The contents on cyclic peptides, as well as purity were subject of only minor fluctuations.

TABLE 4

| | Laboratory Syringe temperature 2 to 8° C. | | Storage container of a nebulizer, temperature 25° C. | |
|---|---|---|---|---|
| Parameter | T = 0 | T = 7 days | T = 0 | T = 24 hours |
| Appearance | clear solution | | clear solution | |
| Amount/contents | 25 mg/ml | | 25 mg/ml | |
| Purity | 96.3% | 96.2% | 96.6% | 96.5% |

An aqueous solution of a cyclic peptide of amino acid sequence SEQ ID NO:1 to SEQ ID NO:6 for inhalation thus is stable in a laboratory commonly used syringe at 2 to 8° C. for 7 days, or in the container of a nebulizer at 25° C. for at least 24 hours.

EXAMPLE 7

Figure 4:
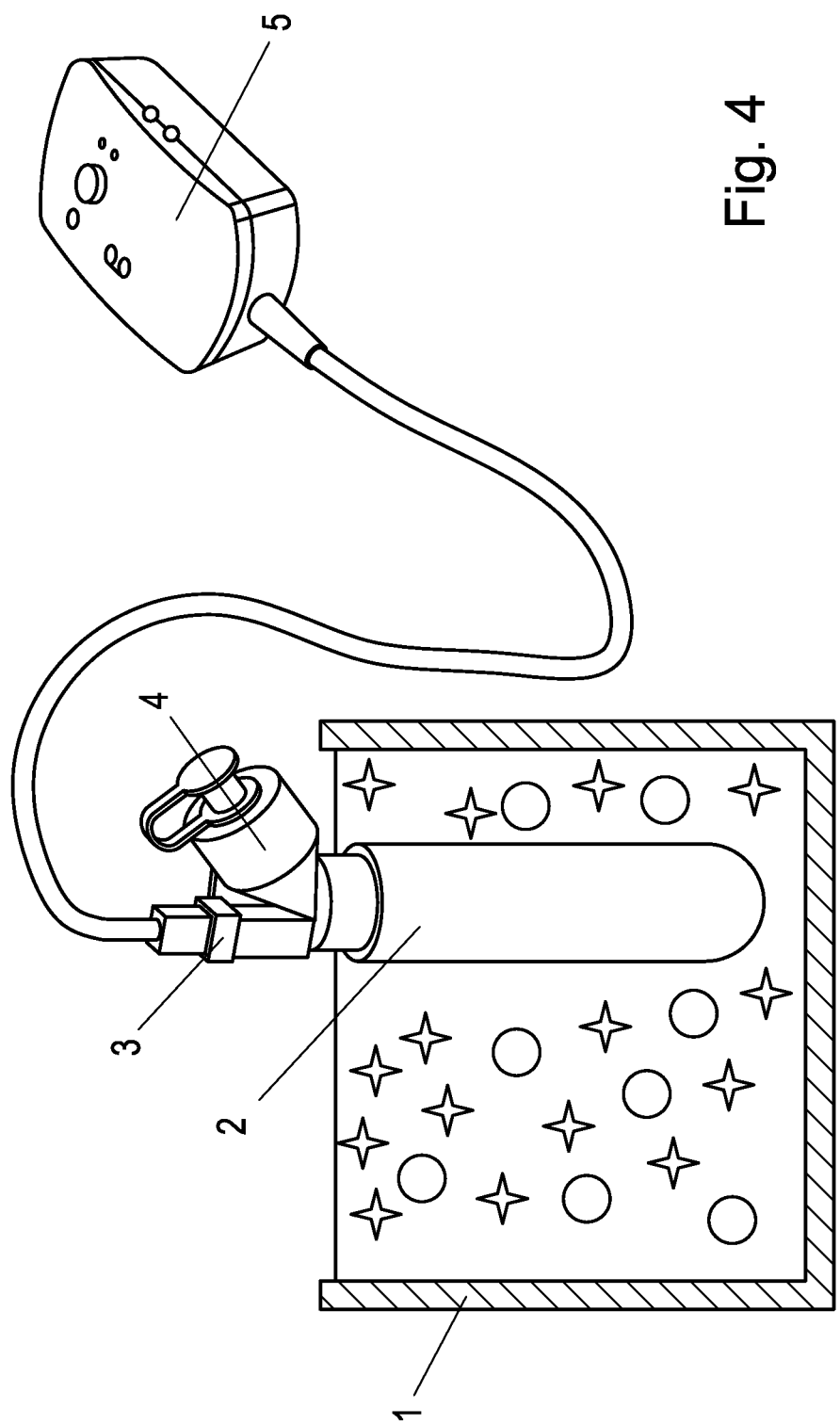
FIG. 4 shows schematically an experimental assembly for condensing aerosol in a cooling trap, wherein
1 denotes a polystyrene container filled with ice and salt,
2 denotes a small tube with the dissolved peptide (control substance),
3 denotes a nebulizer,
4 denotes a store room, and
5 a control module.

Investigation Regarding Stability of the Cyclic Peptides of Amino Acid Sequence SEQ ID NO:1 to SEQ ID NO:6 in Dissolved Preparation During Conversion into an Aerosol Since proteins and peptides occasionally may be rather unstable, it was investigated, whether the cyclic peptides of amino acid sequence SEQ ID NO:1 to SEQ ID NO:6 in dissolved preparation during conversion into an aerosol remain stable. For that the cyclic peptides were dissolved in water as described in example 4. After filling into the storage container of a nebulizer the aqueous solution of the cyclic peptides were converted into an aerosol. For that a "Mesh-Type" nebulizer was used. The aerosol passing out from the nebulizer was collected in a cooling trap as shown in FIG. 4. The biological activity of the collected aerosols was determined by means of the Patch Clamp method. Thereby macroscopic currents of A549 cells were deduced in the "whole cell" configuration of the "Patch-clamp" technique, as described under "Electrophysiological Investigations of the Amilorid-sensitive Sodium Ion Channel (ENaC)".

The chemical stability of the condensed aerosols was determined by means of reverse HPLC/MS.

It could exemplarily be shown that the cyclic peptide of amino acid sequence SEQ ID NO:1 in dissolved preparation during the transformation into an aerosol keeps its biological, as well as its chemical stability.

EXAMPLE 8

Physicochemical Characterisation of the Aerosols of the Cyclic Peptides of Amino Acid Sequence SEQ ID NO:1 to SEQ ID NO:6

By means of a nebulizer which converts aqueous solution into an aerosol, also the aqueous solutions of the cyclic peptides of amino acid sequence SEQ ID NO:1 to SEQ ID NO:6 may be converted into aerosols. Such aerosols can be characterized with respect to the medium droplet size, as well as to size distribution of the aerosol droplets. For that conventional methods are used, which are described also in pharmacopoeias. The one analytical method uses the cascade impactor in its actual construction, the "Next Generation Impactor". Thereby the aerosol is conducted through a series of sieve plates, whereby the diameter of the holes is diminished with each plate and the amount of the holes is increased. In the other analytical method, the laser-diffraction measurement, the droplet sizes are determined by means of laser. The 2 important parameters which are determined during these measurements, one the one hand is the median of the diameter of all droplets, and on the other hand, the amount of droplets having a diameter of ≤5 µm. In the literature that diameter is described as a limit, under which inhaled aerosol particles arrive in fact in the lung.

It is ramblingly known, that in practice from a generated aerosol only a part is available for the patient. Thus, for determining the amount of aerosol which is available for a user, trials with a breathing simulator were carried out. For investigating the particle size and for the implementation of the breathing simulation an aerosol from an aqueous solution of the cyclic peptide of amino acid sequence SEQ ID NO:1 was used. For generating aerosol different nebulizer types were used. The nebulizers A and B were so called "Mesh-Type nebulizers".

Figure 5:
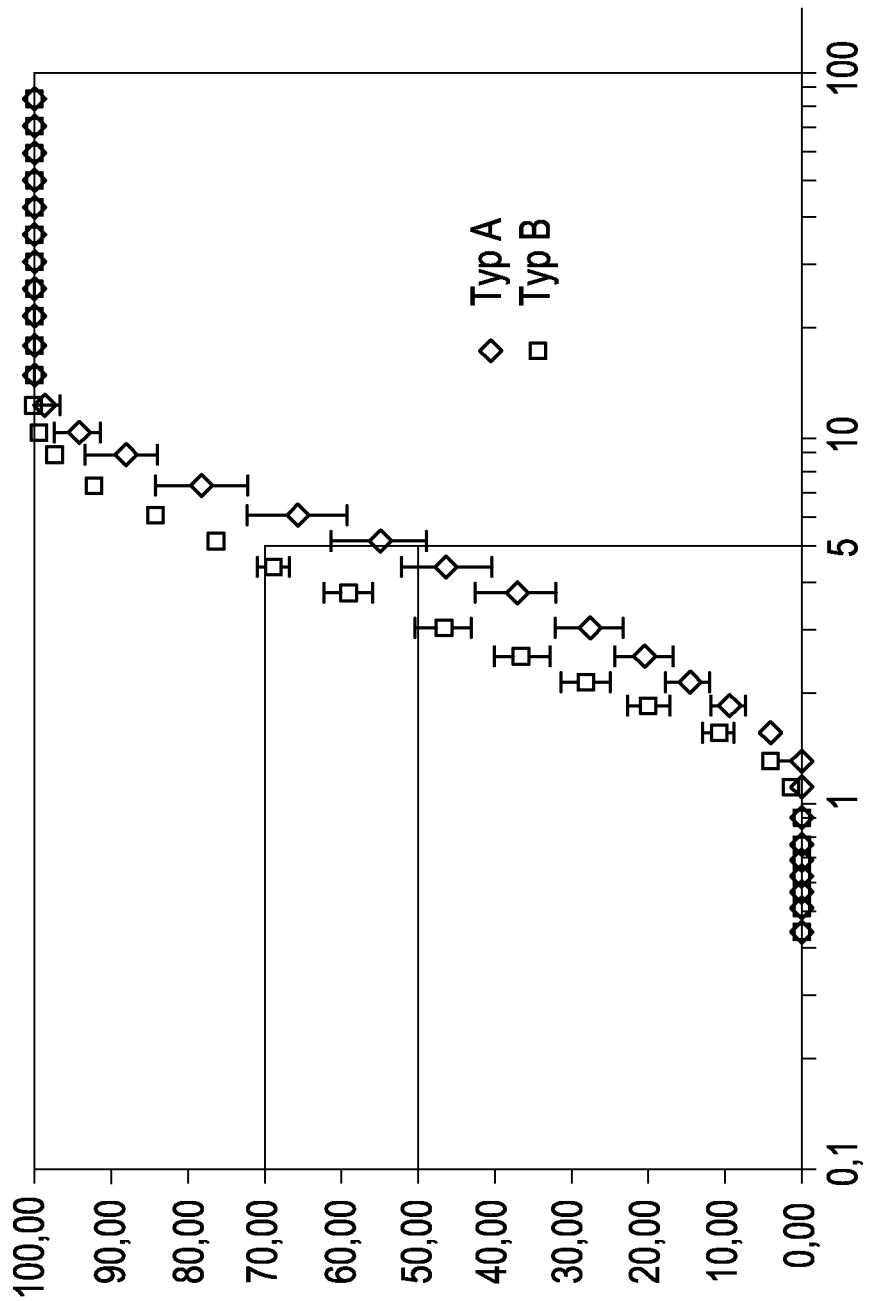
FIG. 5 shows the average particle size distribution of the aerosol of the cyclic peptide with the amino acid sequence SEQ ID NO:1, produced with 2 different nebulizers (type (TYP) A and type (TYP) B). Determination was carried out by means of laser diffraction (flow rate: 15 L/min) Error indicators=SD. The lines show the respective part of particles with diameter of ≤5 μm in the aerosol. on the x-axis the droplet size in μm, on the y-axis the cumulative amount in % is plotted.

The amount of droplets with a diameter of ≤5 µm in the aerosol was in all nebulizers at least 50%, see Table 5 and FIG. 5, wherein characteristics of the aerosol of the cyclic peptide of amino acid sequence SEQ ID NO:1, generated from 3 different nebulizers, are indicated and shown.

TABLE 5

| Nebulizer | Median particle diameter | Amount of particles with Ø ≤5 µm |
|---|---|---|
| Type A | 4.7 µm | 50% |
| Type B | 3.3 µm | 70% |
| Type C | 3.7 µm | 65% |

Figure 6:
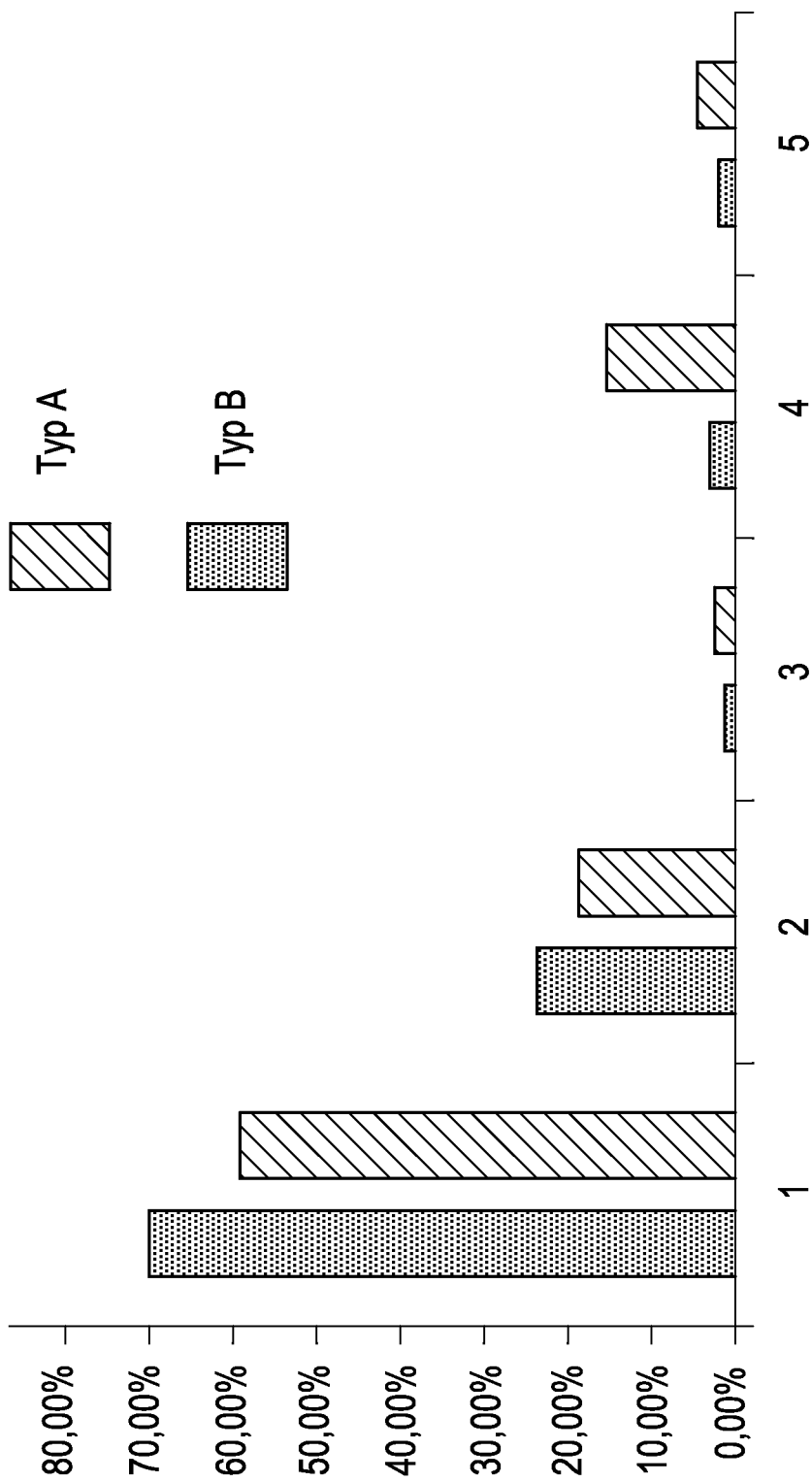
FIG. 6 shows the distribution of the aerosol of the cyclic peptide having the amino acid sequence SEQ ID NO:1 in the breathing simulator at the respective place:
1=inhalation filter
2=exhalation filter
3=filter connection piece
4=nebulizer Y-piece (one-way valve inclusive)
5=residue in the nebulizer
whereby 2 nebulizers, one from type (TYP) A and one from type (TYP) B were used.

Furthermore it could be proven, that the predominant part of the aerosol of an aqueous solution of the cyclic peptide of amino acid sequence SEQ ID NO:1, generated by the nebulizers, is available for inhalation, as shown in FIG. 6, depicted by the quantitative verification of the cyclic protein at the "Inhalation filter". The part of the aerosol which is not available is markedly less (FIG. 6).

EXAMPLE 9

Proof of the Cyclic Peptides of Amino Acid Sequence SEQ ID NO:1 to SEQ ID NO:6 in the Blood after Parenteral Administration The exemplary proof of the cyclic peptides of amino acid sequence SEQ ID NO:1 to SEQ ID NO:6 in the blood after parenteral administration took place in dog and rat. For that exemplarily an aqueous solution of the cyclic peptide of amino acid sequence SEQ ID NO:1 as a bolus (25 mg/kg body weight) was administered intravenously into the experimental animals. Directly after termination of the intravenous application blood was harvested and the concentration of the cyclic protein of amino acid sequence SEQ ID NO:1 was determined by means of common laboratory reverse HPLC/MS. The results are set out in Table 6, wherein the plasma concentration of the cyclic peptide of amino acid sequence SEQ ID NO:1 after intravenous application is indicated.

TABLE 6

|  | Rat | Dog |
|---|---|---|
| Plasma concentration (µg/ml) | 28 | 42 |

EXAMPLE 10

Proof of the Cyclic Peptides of Amino Acid Sequence SEQ ID NO:1 to SEQ ID NO:6 in Lung Tissue after Inhalation as an Aerosol The proof of a cyclic peptide of amino acid sequence SEQ ID NO:1 to SEQ ID NO:6 may take place in lung tissue of rats. For that exemplarily an aerosol was produced with a nebulizer from an aqueous solution of the cyclic peptide of amino acid sequence SEQ ID NO:1. The aerosol was inhaled by the experimental animal (72 mg/kg body weight). After termination of aerosol inhalation, the lung tissue, as well as the blood of the experimental animal was examined. By means of reverse HPLC/MS the concentration of the cyclic peptide of amino acid sequence SEQ ID NO:1 was determined Exemplarily, the cyclic peptide of amino acid sequence SEQ ID NO:1 could be detected in the lung tissue in a concentration of 1.2 µm/g after inhalation of 72 mg/kg body weight in sum. In contrast to that the cyclic peptide of amino acid sequence SEQ ID NO:1 could not be detected in the blood up to a detection limit of 0.1 µm/ml.

EXAMPLE 11

Effect of the Peptides of Amino Acid Sequence SEQ ID NO:1 to SEQ ID NO:7 onto Deglycolized Cell Surfaces In whole cell experiments A549 cells were incubated with the enzyme "PNGase F" (Peptide-$N^4$—(N-acetyl-β-D-glucosaminyl)asparagine Amidase F), 100 units for 1 to 5 minutes, directly before the Patch Clamp measurements and the cover glasses with the cultivated cells were rinsed with external solution, before transferring them into the chamber of the 1 mL bath. After control recordings, 240 nM of the peptide of amino acid sequence SEQ ID NO:1 was added to the bath solution. The total cell current was recorded of cells without any pre-treatment under controlled conditions and after addition of a peptide of amino acid sequence SEQ ID NO:1 to SEQ ID NO:7 at Eh=−100 mV, also as pre-treatment with PNGase F. The results of the deglycosilation experiments under use of the Patch Clamp assays in the whole cell modus shows Table 7, wherein the effect of deglycosilation of A549 cells onto the activation of the sodium current by means of the peptides of amino acid sequence SEQ ID NO:1 to SEQ ID NO:7 is indicated. Whole cell currents were recorded at Eh=−100 mV. The concentration of the peptides of amino acid sequence SEQ ID NO:1 to SEQ ID NO:7 in the bath solution was 240 nM.

TABLE 7

| Control/Peptide | Pre-treatment with PNGase F | No pretreatment with PNGase F |
|---|---|---|
| control | 25.4 pA (n = 16) | |
| SEQ ID NO: 1 | 19.6 pA (n = 3) | 1073.3 ± 15.1 pA |
| SEQ ID NO: 2 | 21.3 pA (n = 3) | (n = 10) |
| SEQ ID NO: 3 | 20.6 pA (n = 3) | |

TABLE 7-continued

| Control/Peptide | Pre-treatment with PNGase F | No pretreatment with PNGase F |
|---|---|---|
| SEQ ID NO: 4 | 22.5 pA (n = 3) | |
| SEQ ID NO: 5 | 22.4 pA (n = 3) | |
| SEQ ID NO: 6 | 19.9 pA (n = 3) | |
| SEQ ID NO: 7 | No activity | No activity |

The cells with PNGase F (treatment) before the Patch Clamp Assay reduced the ability of the peptides of amino acid sequence SEQ ID NO:1 to SEQ ID NO:6 to enhance the sodium current. Under control conditions without addition of peptide into the bath and at a Holding Potential of −100 mV, the sodium current was 25.4 pA, in untreated cells, as well as in cells which were pretreated with PNGase F. In untreated cells resulted the addition of peptides of amino acid sequence SEQ ID NO:1 to SEQ ID NO:6 (end concentration 240 nM) to the bath solution at a Holding Potential of −100 mV in a noticeable sodium current of more than 1,000 pA. In contrast, a peptide of amino acid sequence SEQ ID NO:7 showed no activity.

EXAMPLE 12

Lung Transplantation Experiments with Pigs

Brain-dead pigs were brought into back position and a vertical sternotomy was carried out. The pericardium and both pleural cavities were opened. The lower and upper cavial venes were embraced. An inflow catheter was inserted into the lung artery by means of a purse-string suture in the right ventricular discharging tract. An inflow occlusion was obtained by connecting the lower and upper cavial venes, discharge occlusion by stapling off the aorta. The lungs then were protected by a prophylactic rinsing with cold, isotonic conservation solution (50 ml per kg body weight of the pig, comprising potassium ions, sodium ions, magnesium ions, calcium ions, chloride ions, dextran, glucose, buffer ions) through the inflow catheter. Incision of the left heart tube yields discharge. The lungs were aerated during that time period with 50% oxygen and ice sludge was given into both pleural cavities and into the mediastinum.

The explanation technique in sum was the removal with heart and esophagus according to the following steps:
a) Dissection of the soft tissue bridges to the thoracic cavity at both sides of the trachea.
b) Transsection of both pulmonal ligaments (very deep, difficult exposure), then of VCI, of the low thoracic aorta ascendens, or the esophagus, respectively.
c) Blunt-separation of residual mediastinal adhesions.
d) Entire distension of the donor lung before the tracheal closure with a clip.

After explantation the lungs were winded into gauze, put into an ice bag, filled with low-potassium-dextran-extracellular solution and stored at 4° C. for 18 to 24 hours.

For the ex-vivo lung conditioning the EVLP-technique was used (extravascular lung perfusion). In the EVLP-technique donor lungs are put into a circulation, composed of a pump, aerator and filters. In the EVLP-technique the temperature may be increased up to 37° C. In the EVLP an aerator is used, in order to deliver oxygen to the lungs. The pump is used, to perfuse the lungs with an extracellular solution, containing human albumin and nutrient. During the EVLP the lung function may be assessed regularly regarding key indicators.

For the experimental pig lung transplantation experiment, the EVLP circulation was primed with 2.0 litres human albumin solution. That extracellular solution had an optimal colloidal osmotic pressure. After the circulation was vented, the prime was circulated at 20° C. until it was connected with the lungs. Heparin, Cefuroxim, Methylprednisolon war added to the perfusate.

The processing of the donor lung from the pig was started with sewing on a funnel-shaped tube from Silastic with a pressure-monitored catheter, implemented into the left atrial cuff (LA), for openly splinting the LA and for maintaining a closed perfusion circulation.

That tube was secured anastomosed onto the LA cuff under use of an ongoing 5-0 mMonofilament yarn, in order to achieve a reliable and effective discharging drainage. The same type cannula was used for the transfixion of the lung artery (PA), all spruced up as required, to adjust onto the PA size. A retrograde Back-Table rinsing was carried out under use of 500 ml buffered, extracellular solution. Before fixing the donor lungs into the EVLP circulation, the trachea was opened and direct bronchial sucking off was carried out, in order to clean the airways. An endotracheal tube (size 8 mm I.D.) was introduced into the trachea and was firmly secured with a Numbilicale band. Thereafter the lungs were transferred onto the EVLP circulation unit. First, connection of the LA cannula with the circulation and initiation of a slow, retrograde flow, in order to vent the PA cannula. A soon as venting was complete, the PA cannula was connected with the circulation and anterograde flow of 150 ml/min was initiated with the perfusate at room temperature. In the next 30 minutes the temperature of the perfusate was increased stepwise up to 37° C. As soon as the temperature had reached 32-34° C., mechanical aeration of the donor lungs of the pigs was started, whereby the aeration rate and the rate of the perfusate flow were stepwise increased.

Flow of the EVLP gas transports oxygen to the lungs and delivers carbon dioxide to the inflow perfusate (86% $N_2$, 6% $O_2$, 8% $CO_2$), by means of the gas exchanger membrane it was initiated (start at 0.5 L/min of gas flow and titration based on the inflow perfusate $pCO_2$), the inflow perfusate pressure ($pCO_2$) between 35-45 mm Hg to maintain. At the moment where the lung was fully expanded, a single dose AP301 (1 mg/kg in 5 ml Aqua), under use of a simple liquid standard nebulizer system was given into the donor lung of a pig, ventilated and run through by the EVLP system switching.

During the EVLP experiments that blood flow was determined constant. The following functional parameters were measured every hour and recorded:

Flow Pulmonal artery (PAF): L/min (mean) Pulmonal artery pressure (PAP): mm Hg

Left Atrial pressure(LAP): mm Hg

Pulmonal vascular resistance (PVR=[PAP−LAP]×80/PAF): dynes/sec/cm-5 medium, top-und plateau pressure of the airway (mAwP, peak AwP, platAwP): cm $H_2O$ dynamic compliance (mL/cm $H_2O$)

perfusate gas analysis-inflow (PA) and effluent (PV) $_pO_2$, $_pCO_2$ und pH.

Results

Figure 2A:
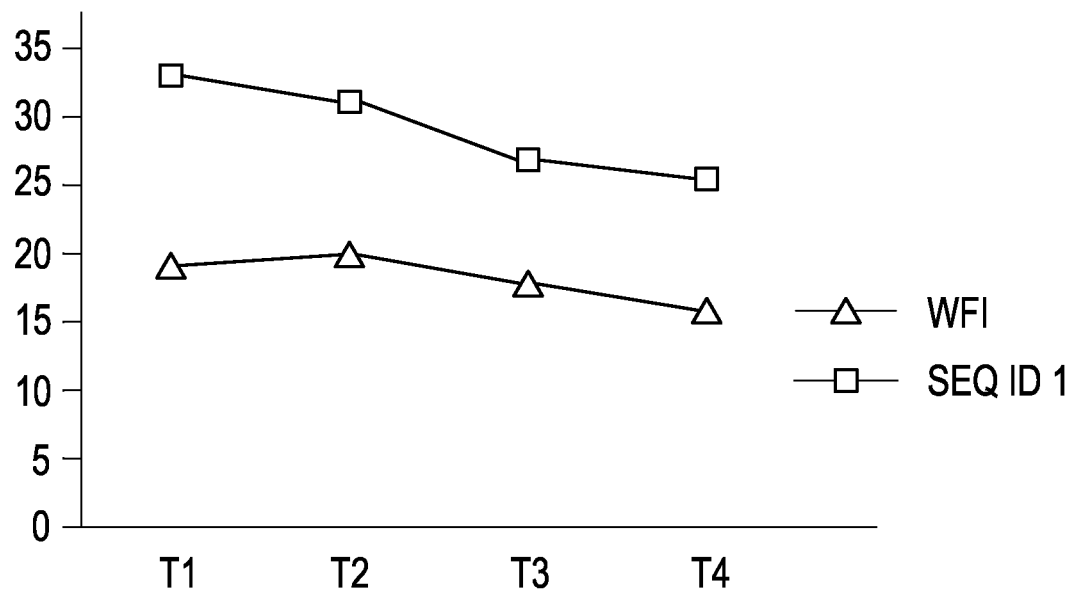
In FIG. 2A on the x-axis time points T1 to T4 are indicated where measurements after inhalative application of the peptide of SEQ ID NO:1 (one time a hour) were made. On the y-axis the compliance is plotted; and in FIG. 2B on the x-axis again the time points T1 to T4 and on the y-axis the arterio-venous pO2 difference ΔpO2. Water for Injection (WFI) was used as a control. Means of 8 experiments per group are shown.
Figure 2B:
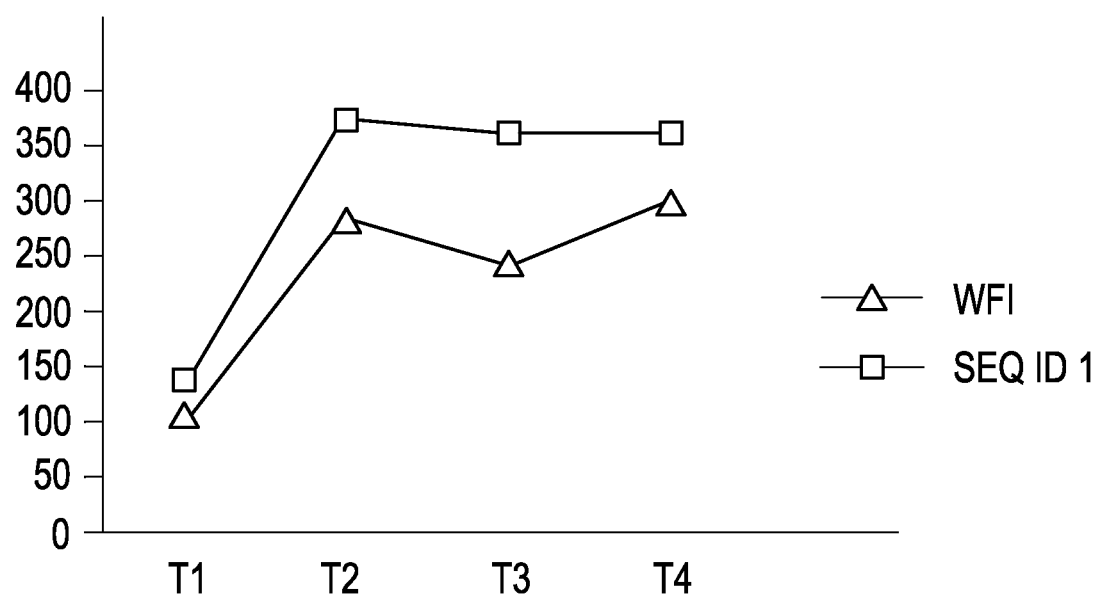
FIG. 2 shows results of inhalative application of the cyclic peptide of SEQ ID NO:1 during a lung perfusion outside of the body (extra-corporal, ex vivo), simulating a lung transplantation.

This study assesses the effects of a peptide having the amino acid sequence SEQ ID NO:1 onto the lung function in an extracorporeal system simulating lung transplantation. Study results showed, that upon administration via inhalation both, the dynamic lung conformity, as well as the arterio-venous $pO_2$ difference $\Delta pO_2$ in lungs, which were treated with a peptide having the amino acid sequence SEQ ID NO:1 were improved, as shown in FIG. 2A and FIG. 2B.

The use of a peptide having the amino acid sequence of SEQ ID NO:7 showed no improving effects regarding the lung.

SEQUENCE LISTING

<160> NUMBER OF SEQ ID NOS: 8

<210> SEQ ID NO 1
<211> LENGTH: 17
<212> TYPE: PRT
<213> ORGANISM: Artificial Sequence
<220> FEATURE:
<223> OTHER INFORMATION: cyclic peptide with disulfide bridge
<220> FEATURE:
<221> NAME/KEY: DISULFIDE
<222> LOCATION: (1)..(17)

<400> SEQUENCE: 1

Cys Gly Gln Arg Glu Thr Pro Glu Gly Ala Glu Ala Lys Pro Trp Tyr
1               5                   10                  15

Cys

<210> SEQ ID NO 2
<211> LENGTH: 19
<212> TYPE: PRT
<213> ORGANISM: Artificial Sequence
<220> FEATURE:
<223> OTHER INFORMATION: cyclic peptide with an amide bond between the
      amine group attached to the epsilon-C-atom of the lysine residue
      and the carboxy group bound to the gamma-C-atom of the side chain
      of the glutaminic acid residue

<400> SEQUENCE: 2

Lys Ser Pro Gly Gln Arg Glu Thr Pro Glu Gly Ala Glu Ala Lys Pro
1               5                   10                  15

Trp Tyr Glu

<210> SEQ ID NO 3
<211> LENGTH: 17
<212> TYPE: PRT
<213> ORGANISM: Artificial Sequence
<220> FEATURE:
<223> OTHER INFORMATION: cyclic peptide with an amide bond between the
      amine group attached to the epsilon-C-atom of the side chain of
      the lysine residue and the carboxy group of the glycine residue

<400> SEQUENCE: 3

Lys Gly Gln Arg Glu Thr Pro Glu Gly Ala Glu Ala Lys Pro Trp Tyr
1               5                   10                  15

Gly

<210> SEQ ID NO 4
<211> LENGTH: 17
<212> TYPE: PRT
<213> ORGANISM: Artificial Sequence
<220> FEATURE:
<223> OTHER INFORMATION: cyclic peptide with an amide bond between the
      amine group bound to the delta-C-atom of the side chain of the
      ornithine residue and the carboxy group of the glycine residue
<220> FEATURE:
<221> NAME/KEY: MOD_RES
<222> LOCATION: (1)..(1)
<223> OTHER INFORMATION: X = Ornithine

<400> SEQUENCE: 4

Xaa Gly Gln Arg Glu Thr Pro Glu Gly Ala Glu Ala Lys Pro Trp Tyr
1               5                   10                  15

Gly

<210> SEQ ID NO 5
<211> LENGTH: 17

```
<212> TYPE: PRT
<213> ORGANISM: Artificial Sequence
<220> FEATURE:
<223> OTHER INFORMATION: cyclic peptide with an amide bond between the
      amine group of the 4-amino butyric acid and the carboxy group
      bound to beta-C-atom of of the side chain of the asparaginic acid
<220> FEATURE:
<221> NAME/KEY: MOD_RES
<222> LOCATION: (1)..(1)
<223> OTHER INFORMATION: X = 4-Amino butyric acid

<400> SEQUENCE: 5

Xaa Gly Gln Arg Glu Thr Pro Glu Gly Ala Glu Ala Lys Pro Trp Tyr
 1               5                  10                  15

Asp

<210> SEQ ID NO 6
<211> LENGTH: 17
<212> TYPE: PRT
<213> ORGANISM: Artificial Sequence
<220> FEATURE:
<223> OTHER INFORMATION: cyclic peptide with an amide bond between the
      amine group of the beta-alanine residue and the carbonyl group
      bound to the gamma-C-atom of the glutaminic acid residue
<220> FEATURE:
<221> NAME/KEY: MOD_RES
<222> LOCATION: (1)..(1)
<223> OTHER INFORMATION: X = beta-alanine

<400> SEQUENCE: 6

Xaa Gly Gln Arg Glu Thr Pro Glu Gly Ala Glu Ala Lys Pro Trp Tyr
 1               5                  10                  15

Glu

<210> SEQ ID NO 7
<211> LENGTH: 17
<212> TYPE: PRT
<213> ORGANISM: Artificial Sequence
<220> FEATURE:
<223> OTHER INFORMATION: cyclic peptide with disulfide bridge
<220> FEATURE:
<221> NAME/KEY: DISULFIDE
<222> LOCATION: (1)..(17)

<400> SEQUENCE: 7

Cys Gly Gln Arg Glu Ala Pro Ala Gly Ala Ala Ala Lys Pro Trp Tyr
 1               5                  10                  15

Cys

<210> SEQ ID NO 8
<211> LENGTH: 17
<212> TYPE: PRT
<213> ORGANISM: Artificial Sequence
<220> FEATURE:
<223> OTHER INFORMATION: cyclic peptide of formula I
<220> FEATURE:
<221> NAME/KEY: MOD_RES
<222> LOCATION: (1)..(1)
<223> OTHER INFORMATION: X = selectd from Cys; Lys-Ser-Pro; Lys;
      ornithine; 4-amino butyric acid; beta-alanine
<220> FEATURE:
<221> NAME/KEY: MOD_RES
<222> LOCATION: (17)..(17)
<223> OTHER INFORMATION: X = ausgew?hlt aus Cys; Asp; Gly, Glu
```

```
<400> SEQUENCE: 8

Xaa Gly Gln Arg Glu Thr Pro Glu Gly Ala Glu Ala Lys Pro Trp Tyr
1               5                   10                  15

Xaa
```

The invention claimed is:

1. An aqueous aerosol for inhalation generated by nebulization, the aqueous aerosol consisting of:
   water; and
   a cyclic peptide of formula I, or a salt thereof with a proviso that the salt excludes a trifluoroacetate ion, dissolved in the water:

$$X_1\text{-GQRETPEGAEAKPWY-}X_2, \quad \text{I}$$

wherein
   $X_1$ comprises an amino acid sequence, with 1 to 4 members, comprising natural and unnatural amino acids, and
   $X_2$ comprises a natural amino acid, and wherein
   $X_1$ comprises the N-terminal amino acid in position 1 on the left in formula I, and $X_2$ comprises the C-terminal amino acid in the ultimate, right position in formula I,
   wherein the cyclic peptide is in the form of a lyophilisate prior to mixing with the water,
   wherein the aqueous aerosol includes particles of the water and the cyclic peptide, the particles having a diameter less than or equal to 5 μm,
   wherein the cyclic peptide, when in solution, remains fully active for a period of at least 7 days, and
   wherein the cyclic peptide, when in a lyophilized form, remains fully active at room temperature for a period of at least 6 months.

2. The aqueous aerosol of claim 1, wherein $X_1$ in formula I is selected from the amino acid (sequence) C (Cys), KSP (Lys-Ser-Pro), K (Lys), ornithine, 4-amino butyric acid, and β-alanine.

3. The aqueous aerosol of claim 1, wherein $X_2$ in formula I is selected from the group C (Cys), D (Asp), G (Gly) and E (Glu).

4. The aqueous aerosol of claim 1, wherein the cyclic compound of formula I is selected from a peptide of the amino acid sequences SEQ ID NO: 1
Cyclo(CGQRETPEGAEAKPWYC)

wherein a disulfide bridge is formed between both of the terminal cysteine residues;

SEQ ID NO: 2
Cyclo(KSPGQRETPEGAEAKPWYE)

wherein an amide bond is formed between the amine group which is attached to the ε-carbon atom of the N-terminal lysine residue and the side chain carboxy group, attached to the y-carbon atom of the C-terminal glutamic acid residue;

SEQ ID NO: 3
Cyclo(KGQRETPEGAEAKPWYG)

wherein an amide bond is formed between the amine group which is attached to the ε-carbon atom of the side chain of the N-terminal lysine residue with the carboxy group of the C-terminal glycine residue;

SEQ ID NO: 4
Cyclo(ornithine-GQRETPEGAEAKPWYG)

wherein an amide bond is formed between the amine group which is attached to the σ-carbon atom of the side chain of the N-terminal ornithine residue and the carboxy group of the C-terminal glycine residue;

SEQ ID NO: 5
Cyclo(4-amino butyric acid-GQRETPEGAEAKPWYD)

wherein an amide bond is formed between the amine group of the N-terminal 4-amino butyric acid residue and the side chain carboxy group which is attached to the β-carbon atom of the C-terminal aspartic acid residue; and SEQ ID NO: 6
Cyclo(β-alanine-GQRETPEGAEAKPWYE), wherein an amide bond is formed between the amine group of the N-terminal β-alanine residue (3-amino propanoic acid residue) and the side chain carboxy group, which is attached to the y-carbon atom of the C-terminal glutamic acid residue.

5. An extracorporeal method of conditioning/improving lung functions, comprising spraying a donor lung ex vivo with the aqueous aerosol of claim 1.

6. An aqueous aerosol for inhalation generated by nebulization, the aqueous aerosol consisting of:
   water; and
   a cyclic peptide of formula I in the form of a hydrochloride salt, dissolved in the water:

$$X_1\text{-GQRETPEGAEAKPWY-}X_2, \quad \text{I}$$

wherein
   $X_1$ comprises an amino acid sequence, with 1 to 4 members, comprising natural and unnatural amino acids, and
   $X_2$ comprises a natural amino acid, and wherein
   $X_1$ comprises the N-terminal amino acid in position 1 on the left in formula I, and $X_2$ comprises the C-terminal amino acid in the ultimate, right position in formula I,
   wherein the cyclic peptide is in the form of a lyophilisate prior to mixing with the water, wherein the cyclic peptide remains fully active in solution for a period of at least 7 days and remains fully active when in a lyophilized form for a period of at least 6 months at room temperature, and
wherein the aqueous aerosol includes particles of the water and the cyclic peptide, the particles having a diameter less than or equal to 5 µm.

7. An aqueous aerosol for inhalation generated by nebulization, comprising:
water, and
a cyclic peptide of formula I, or a salt thereof with a proviso that the salt excludes a trifluoroacetate ion, dissolved in the water:

I
$X_1$-GQRETPEGAEAKPWY-$X_2$, wherein
$X_1$ comprises an amino acid sequence, with 1 to 4 members, comprising natural and unnatural amino acids, and
$X_2$ comprises a natural amino acid, and wherein
$X_1$ comprises the N-terminal amino acid in position 1 on the left in formula I, and $X_2$ comprises the C-terminal amino acid in the ultimate, right position in formula I,
wherein the cyclic peptide is in the form of a lyophilisate without additives and/or stabilizers prior to mixing with the water, the additives and/or stabilizers comprising one or more of tensides, buffer mixtures, lipid admixtures, albumin, osmotic agents, antioxidants, aggregation and/or precipitation prevention agents, liposomes, gelatine, alginates, or sugars,
wherein the aqueous aerosol includes particles of the water and the cyclic peptide, the particles having a diameter less than or equal to 5 µm,
wherein the cyclic peptide when in a lyophilized form remains fully active for a period of at least 7 days,
wherein the cyclic peptide when in a lyophilized form remains fully active at room temperature for a period of at least 6 months, and
wherein the aqueous aerosol is without additives and/or stabilizers after mixing with the water.

8. The aqueous aerosol of claim 7, wherein $X_1$ in formula I is selected from the amino acid (sequence) C (Cys), KSP (Lys-Ser-Pro), K (Lys), ornithine, 4-amino butyric acid, and β-alanine.

9. The aqueous aerosol of claim 7, wherein $X_2$ in formula I is selected from the group C (Cys), D (Asp), G (Gly) and E (Glu).

10. The aqueous aerosol of claim 7, wherein the cyclic compound of formula I is selected from a peptide of the amino acid sequences SEQ ID NO: 1
Cyclo(CGQRETPEGAEAKPWYC)

wherein a disulfide bridge is formed between both of the terminal cysteine residues;

SEQ ID NO: 2
Cyclo(KSPGQRETPEGAEAKPWYE)

wherein an amide bond is formed between the amine group which is attached to the ε-carbon atom of the N-terminal lysine residue and the side chain carboxy group, attached to the γ-carbon atom of the C-terminal glutamic acid residue;

SEQ ID NO: 3
Cyclo(KGQRETPEGAEAKPWYG)

wherein an amide bond is formed between the amine group which is attached to the ε-carbon atom of the side chain of the N-terminal lysine residue with the carboxy group of the C-terminal glycine residue;

SEQ ID NO: 4
Cyclo(ornithine-GQRETPEGAEAKPWYG)

wherein an amide bond is formed between the amine group which is attached to the σ-carbon atom of the side chain of the N-terminal ornithine residue and the carboxy group of the C-terminal glycine residue;

SEQ ID NO: 5
Cyclo(4-amino butyric acid-GQRETPEGAEAKPWYD)

wherein an amide bond is formed between the amine group of the N-terminal 4-amino butyric acid residue and the side chain carboxy group which is attached to the β-carbon atom of the C-terminal aspartic acid residue; and SEQ ID NO: 6
Cyclo(β-alanine-GQRETPEGAEAKPWYE), wherein an amide bond is formed between the amine group of the N-terminal β-alanine residue (3-amino propanoic acid residue) and the side chain carboxy group, which is attached to the γ-carbon atom of the C-terminal glutamic acid residue.

11. A method of preparing an aqueous aerosol for inhalation wherein the aerosol includes particles of the water and a cyclic peptide of formula I, or a salt thereof with a proviso that the salt excludes a trifluoroacetate ion:

I
$X_1$-GQRETPEGAEAKPWY-$X_2$, wherein
$X_1$ comprises an amino acid sequence, with 1 to 4 members, comprising natural and unnatural amino acids, and
$X_2$ comprises a natural amino acid, and wherein
$X_1$ comprises the N-terminal amino acid in position 1 on the left in formula I, and $X_2$ comprises the C-terminal amino acid in the ultimate, right position in formula I,
comprising the steps of:
preparing a lyophilisate of the cyclic peptide of formula I free of stabilizers and additives;
mixing the lyophilisate with water; and
generating the aqueous aerosol by nebulization, wherein the aqueous aerosol is generated without stabilizers and additives and includes particles of the water and the cyclic peptide, the particles having a diameter less than or equal to 5 µm.

* * * * *

UNITED STATES PATENT AND TRADEMARK OFFICE
CERTIFICATE OF CORRECTION

PATENT NO. : 10,711,041 B2
APPLICATION NO. : 14/784926
DATED : July 14, 2020
INVENTOR(S) : Fischer et al.

Page 1 of 2

It is certified that error appears in the above-identified patent and that said Letters Patent is hereby corrected as shown below:

In the Specification

Column 1
Line 9, change "mode how" to –mode of how–

Column 2
Line 41, change "invention". A" to –invention. A–
Line 44, change "invention"." to –invention.–

Column 4
Line 30, change "normal" to –normally–
Line 37, change "In biological environment" to –In a biological environment,–
Line 40, change "in form" to –in the form–
Line 45, change "In biological environment" to –In a biological environment,–
Line 63, change "In case" to –In the case–
Line 66, change "cyclicd" to –cyclic–
Line 67, change "according" to –accordingly–

Column 6
Lines 56-57, change "it came" to –it became–

Column 8
Lines 56-57, change "in dependence" to –independent–

Column 12
Line 54, change "of" to –to–

Column 13
Line 30, change "still fully was" to –was still fully–
Line 60, change "not always can" to –cannot always–

Signed and Sealed this
Sixth Day of October, 2020

Andrei Iancu
*Director of the United States Patent and Trademark Office*

Column 14
Line 9, change "of" to –to–

Column 15
Line 12, change first instance of "one" to –on–
Line 24, change "generating aerosol" to –generating an aerosol–

Column 17
Line 34, change "venes" to –veins–

Column 18
Line 2, change "war" to –were–
Line 9, change "secured" to –securely–
Line 51, change "und" to –and–
Line 55, change "und" to –and–